United States Patent
Matsui et al.

(10) Patent No.: US 10,175,164 B2
(45) Date of Patent: Jan. 8, 2019

(54) DETECTING ECHINOCYTES IN BLOOD

(75) Inventors: Eriko Matsui, Tokyo (JP); Tomohiro Hayakawa, Saitama (JP); Suguru Dowaki, Kanagawa (JP); Hirokazu Tatsuta, Tokyo (JP); Takeshi Kunihiro, Kanagawa (JP)

(73) Assignee: Sony Corporation, Tokyo (JP)

( * ) Notice: Subject to any disclaimer, the term of this patent is extended or adjusted under 35 U.S.C. 154(b) by 716 days.

(21) Appl. No.: 13/565,032

(22) Filed: Aug. 2, 2012

(65) Prior Publication Data
US 2013/0040337 A1 Feb. 14, 2013

(30) Foreign Application Priority Data

Aug. 8, 2011 (JP) .................................. 2011-172741

(51) Int. Cl.
C12M 1/42 (2006.01)
G01N 21/31 (2006.01)
G01N 21/33 (2006.01)

(52) U.S. Cl.
CPC ............. G01N 21/31 (2013.01); G01N 21/33 (2013.01); *G01N 2021/3144* (2013.01); *G01N 2021/3155* (2013.01)

(58) Field of Classification Search
CPC ... G01N 2021/3144; G01N 2021/3155; G01N 21/31; G01N 21/33
See application file for complete search history.

(56) References Cited

U.S. PATENT DOCUMENTS

| | | | | |
|---|---|---|---|---|
| 2004/0054270 A1* | 3/2004 | Pewzner | ............ | A61B 5/14553 600/341 |
| 2005/0037505 A1* | 2/2005 | Samsoondar | ................... | 436/80 |
| 2005/0234315 A1* | 10/2005 | Mayevsky | ........... | A61B 5/0059 600/310 |

OTHER PUBLICATIONS

Kopn et al. (1983) J. Physiol. 339: 573-584.*
J. G. White, MD, "Effects of an Ionophore, A23187, on the Surface Morphology of Normal Erythrocytes," American Journal of Pathology, 1974, vol. 77, No. 3, pp. 507-518.

* cited by examiner

*Primary Examiner* — Lisa J Hobbs
(74) *Attorney, Agent, or Firm* — Chip Law Group

(57) ABSTRACT

As a result of acquiring visible absorption spectra of red blood cells and analyses of the spectra, inventors of the present disclosure have discovered the fact that echinocytes show a characteristic spectrum pattern having an absorption peak in a wavelength region of 450 to 490 nm between Soret and Q bands. Then, the present disclosure provides a blood analysis apparatus having an analysis section for detecting the absorption peak of a visible absorption spectrum acquired for blood. In accordance with this blood analysis apparatus, on the basis of the absorption peak, it is possible to detect echinocytes contained in blood.

7 Claims, 2 Drawing Sheets

DETECTING ECHINOCYTES IN BLOOD

BACKGROUND

In general, the present disclosure relates to a blood analysis apparatus and a blood analysis method. To put it in more detail, the present disclosure relates to a blood analysis apparatus for detecting echinocytes contained in blood and relates to a blood analysis method for the apparatus.

A process of generating a number of protrusions on the surface of a red blood cell is referred to as a serration. An echinocyte is one result of the serration. 10 to 30 protrusions exist on an echinocyte. The edge of each protrusion is sharp-pointed. The distribution of the protrusions and their lengths are all but uniform.

Some echinocytes exist also in the blood of a healthy person. It is known, however, that some diseases increase the number of echinocytes existing in the blood. Typical diseases increasing the number of echinocytes existing in the blood include the liver function disorder, uremia and gastric cancer. In addition, when taking an immune suppressing drug or after transfusion of stored red blood cells, the number of echinocytes existing in the blood also increases in some cases. On top of that, with regard to the stored blood, when the concentration of the EDTA (Ethylene Diamine Tetra Acetate) is too high or the storage time has been long, it is known that the red blood cells are subjected to the serration.

With regard to the echinocyte, "Effects of an Ionophore, A23187, on the Surface Morphology of Normal Erythrocytes," American Journal of Pathology, 1974, Vol. 77, No. 3, pp. 507-518 (hereinafter referred to as Non-patent Document 1) reports the fact that echinocytes have been obtained by processing a type of an ionophore, which selectively passes on divalent cations to a biological film, in red blood cells. In this case, the type of the ionophore is A23187.

SUMMARY

According to an embodiment of the present disclosure, there is provided a new apparatus for detecting echinocytes contained in blood and a new method provided for the apparatus to serve as a method for detecting echinocytes contained in blood.

As a result of acquiring visible absorption spectra of red blood cells and analyses of the spectra, inventors of the present disclosure have discovered the fact that echinocytes show a characteristic spectrum pattern having an absorption peak in the vicinity of a wavelength of 470 nm, and have completely developed the present disclosure based on the discovery. Since this absorption peak appears as a characteristic of the echinocyte, the echinocyte contained in blood can be detected on the basis of the absorption peak.

That is to say, the present disclosure provides a blood analysis apparatus including an analysis section configured to detect a peak appearing between Soret and Q absorption bands of a visible absorption spectrum acquired for blood.

On top of that, the present disclosure also provides a blood analysis method including detecting a peak appearing between Soret and Q absorption bands of a visible absorption spectrum acquired for blood.

In accordance with the present disclosure, it is possible to provide a new apparatus for detecting echinocytes contained in blood and a new method provided for the apparatus to serve as a method for detecting echinocytes contained in the blood.

DETAILED DESCRIPTION OF THE PREFERRED EMBODIMENT

A preferred embodiment of the present disclosure is explained by referring to the diagrams as follows. It is to be noted that the embodiment explained below is merely a typical implementation of the present disclosure. Thus, the embodiment is not to be interpreted in a narrow sense as a limitation of the range of the present disclosure.

Figure 1:
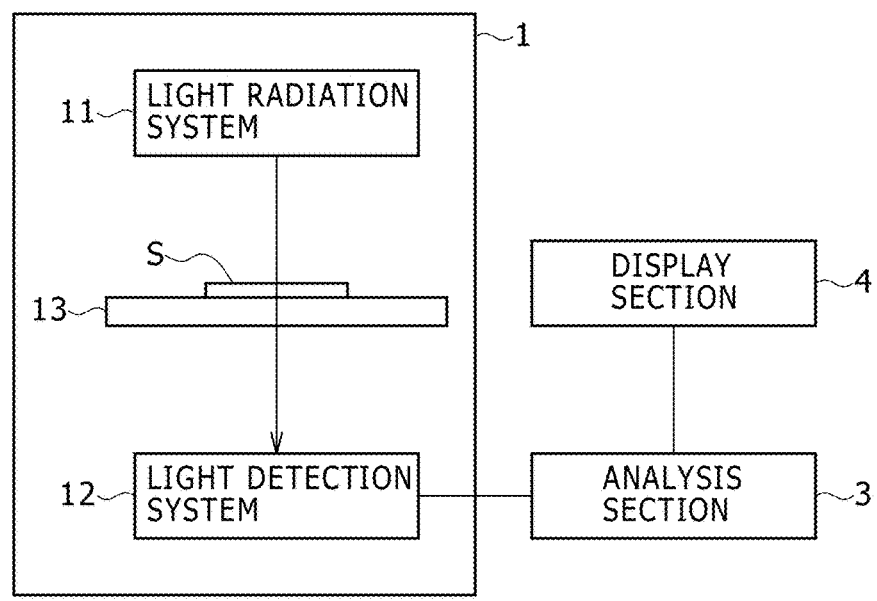
FIG. 1 is an explanatory model diagram showing the configuration of a blood analysis apparatus according to an embodiment of the present disclosure.

The blood analysis apparatus according to the embodiment of the present disclosure can be configured as a combination of an ordinary phase-difference microscope and a two-dimensional visible spectroscope. The blood analysis apparatus includes a light radiation system 11 for radiating white light in order to scan a blood sample S and a light detection system 12 for detecting light transmitted or reflected by the blood sample S in order to acquire a visible absorption spectrum of blood represented by the blood sample S. FIG. 1 is an explanatory model diagram showing the configuration of the blood analysis apparatus according to the present disclosure. The light radiation system 11 is configured to include a light source, a mirror and a lens. On the other hand, the light detection system 12 is configured to include a lens, a diffraction device, a slit, a mirror and an imaging device such as a CCD (charge-coupled device) or a CMOS (complementary metal-oxide semiconductor). The light radiation system 11 and the light detection system 12 compose a measurement section 1.

The blood analysis apparatus also has an analysis section 3 for detecting a peak appearing in a wavelength region of 450 to 490 nm included in a visible absorption spectrum acquired for the blood as a wavelength region between a Soret absorption band and a Q absorption band. In the following description, the visible absorption spectrum acquired for blood is also referred to as a measured spectrum. It is more desirable that the wavelength of the detected peak is approximately 470 nm. Since this absorption peak appears as a characteristic of the echinocyte, the echinocyte contained in the blood can be detected on the basis of the absorption peak. Reference numeral 4 shown in the figure denotes a display section for displaying a result of detection of the absorption peak or a result of detection of the echinocyte. The display section is typically a display unit or a printer.

The measured spectrum exhibiting the detected peak as a characteristic of the echinocyte is compared with a standard spectrum in order to identify a difference in spectrum shape. The standard spectrum is a visible absorption spectrum stored in advance as a spectrum for red blood cells each having an ordinary disk shape. The standard spectrum may have been stored from the beginning in the analysis section 3 or may have been stored so as to be transferred to the analysis section 3 from a memory external to the analysis section 3.

The blood analysis apparatus according to the embodiment of the present disclosure can be used typically as an extracorporeal circulation dialysis machine, a blood gas inspection apparatus, a blood clotting evaluation apparatus or an occult blood tester, to mention a few. In addition, the blood analysis apparatus can also be used for the purpose of monitoring a drug therapy.

For the purpose of an analysis carried out by making use of the blood analysis apparatus according to the embodiment of the present disclosure to analyze a blood sample taken from an examinee, the apparatus is provided with a sample holding section denoted by reference numeral 13 in the figure. The blood sample is held at such a location on the sample holding section 13 that white light emitted by the light radiation system is radiated to the sample and light transmitted or reflected by the sample is introduced to the light detection system. The sample holding section 13 is typically a stage used for mounting a piece of slide glass to which the blood sample is applied. Such a piece of slide glass is also used in an ordinary microscope.

As an alternative, the sample holding section 13 can also be designed into a configuration in which a portion of a blood holding pack is typically repressed hard thereon. In the configuration, this portion serving as a member is held in such a way that light radiated from the light radiation system is capable of passing through the member. As will be described in the following example, even in the case of morphologically normal red blood cells, all red blood cells exhibiting an absorption peak in the vicinity of a wavelength of 470 nm become echinocytes after the lapse of a certain time. Thus, if stored blood is analyzed by adoption of the blood analysis method according to the embodiment of the present disclosure, at a stage before the appearance of the echinocytes is verified morphologically, it is possible to detect an abnormality of the red blood cells and a deterioration of the stored blood at the molecular level.

In addition, in an analysis carried out by making use of the blood analysis apparatus according to the embodiment of the present disclosure to analyze blood in the body of an examinee, the light radiation system and the light detection system which are employed in the blood analysis apparatus are configured to be respectively capable of radiating white light to a tracheole of a mucosal membrane such as the membrane of the conjunctiva, the nose or the mouth mucosa and capable of converging light reflected by the tracheole. This configuration can adopt a method for radiating light and guiding the light to the surface of the mucosal membrane by making use of typically an optical fiber and for converging light reflected by the mucosal membrane.

It is to be noted that the present disclosure can be realized into the following implementations:

(1) A blood analysis apparatus including an analysis section configured to detect a peak appearing between the Soret and Q absorption bands of a visible absorption spectrum acquired for blood.

(2) The blood analysis apparatus according to implementation (1), wherein the analysis section detects a peak appearing in a wavelength region of 450 to 490 nm.

(3) The blood analysis apparatus according to implementation (2), wherein the analysis section determines whether or not echinocytes exist in the blood on the basis of whether or not the peak has been detected.

(4) The blood analysis apparatus according to implementation (2) or (3), further including a display section configured to display a result of determination as to whether or not the peak has been detected and/or a result of determination as to whether or not the echinocytes exist in the blood.

(5) The blood analysis apparatus according to any one of implementations (1) to (4), further including a measurement section configured to have a light radiation system for radiating visible light to the blood and a light detection system for acquiring a visible absorption spectrum of the blood.

EXAMPLE

Figure 2:
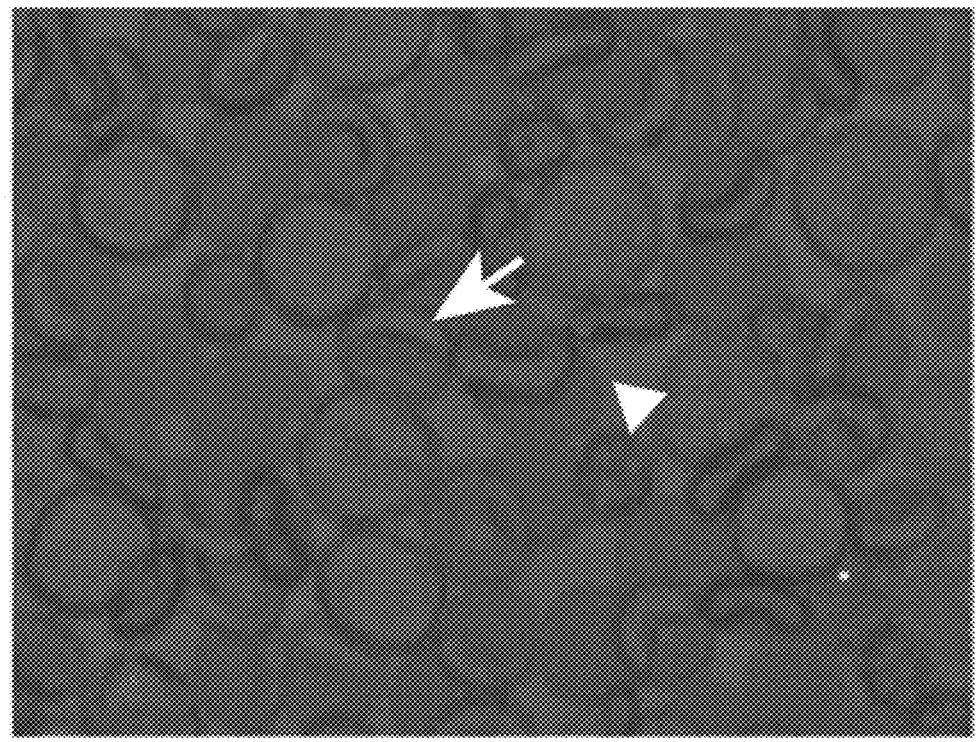
FIG. 2 is a picture showing photographed red blood cells in an example.
Figure 3A:
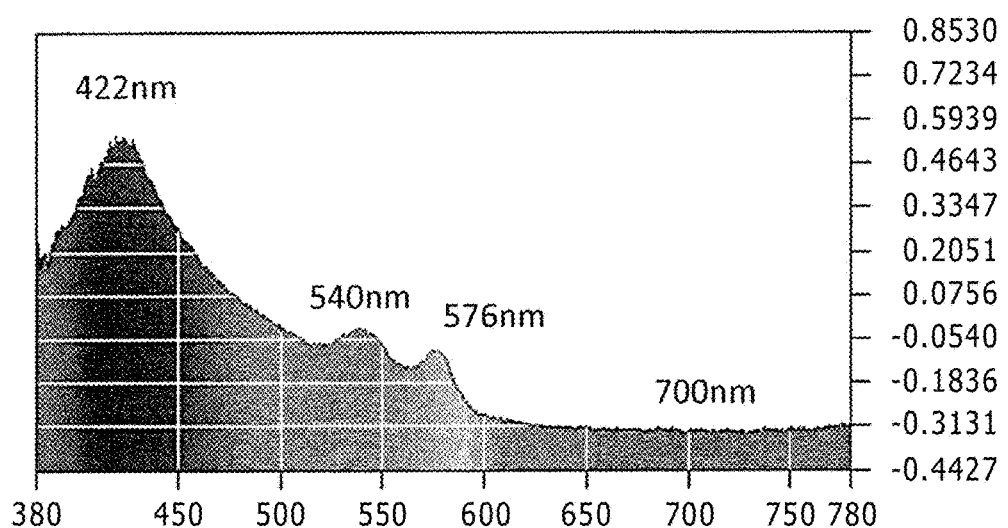
FIGS. 3A and 3B are diagrams each showing a visible absorption spectrum acquired for the red blood cells in the example.
Figure 3B:
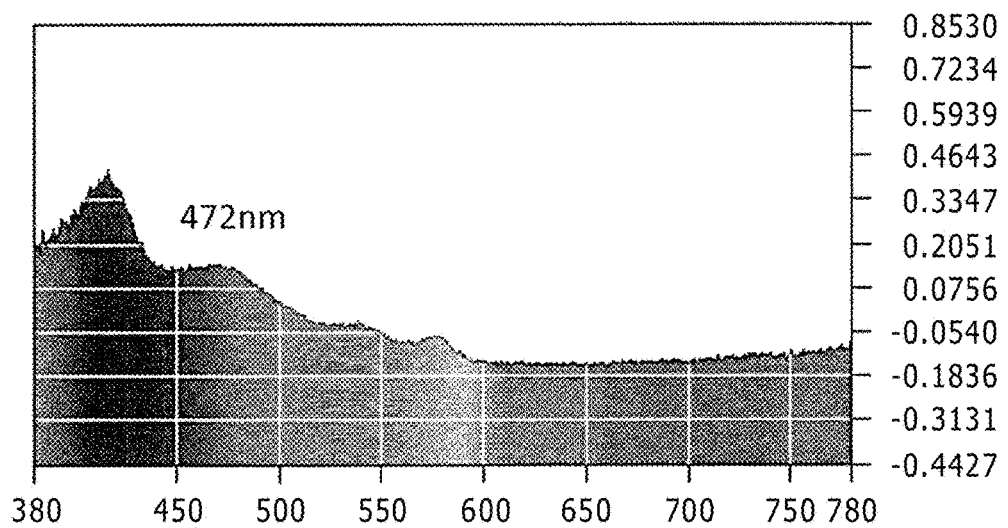

Red blood cells were observed by making use of a phase difference microscope TE2000 made by Nikon corporation and a two-dimensional visible spectroscope made by our company. The red blood cells had been subjected to serration by processing the A23187 ionophore in accordance with a method disclosed in Non-patent Document 1 described earlier. FIG. 2 is a picture showing photographed red blood cells whereas FIGS. 3A and 3B are diagrams each showing a visible absorption spectrum acquired for the red blood cells. It is to be noted that the impossibility to detect an absorption peak from only buffering liquid used in the suspension of the red blood cells was verified.

An arrow shown in FIG. 2 points to a red blood cell having a normal disc shape. FIG. 3A shows a visible absorption spectrum acquired for this red blood cell having a normal disc shape. It is known that hemoglobin is composed of a heme iron complex (heme) and globin whereas the heme iron complex is derived from porphyrin encircling iron. In addition, the heme iron complex exhibits an absorption spectrum having a Soret absorption band in the vicinity of a wavelength of 400 nm and a Q absorption band in the vicinity of a wavelength of 550 nm as a characteristic. Also in the spectrum shown in FIG. 3A, it is obvious that a peak exists at a wavelength of 422 nm in the Soret absorption band whereas peaks exist at wavelengths of 540 nm and 576 nm in the Q absorption band.

On the other hand, a triangle shown in FIG. 2 indicates an echinocyte whereas FIG. 3B shows a visible absorption spectrum acquired for this echinocyte. It has been verified that, the visible absorption spectrum shown in FIG. 3B has a characteristic absorption peak appearing at a wavelength of 472 nm between the Soret absorption band and the Q absorption band. This absorption peak is always detected at the protruding edge of an echinocyte, but also detected in some red blood cells having a normal shape. However, every normally shaped red blood cell from which an absorption peak has been detected changes to an echinocyte after the lapse of a certain time.

It is obvious from these results that a characteristic absorption peak appearing in the vicinity of a wavelength of 470 nm between the Soret absorption band and the Q absorption band can be used as a criterion as to whether or not an echinocyte exists. This absorption peak peculiar to the echinocyte is presumed to reflect a heme structure distortion caused by a change of a relative location of the globin. In this case, the relative location implies a location occupied by the globin as a location relative to the heme iron complex whereas the change of the relative location is a change caused by a variation of the structure of the globin.

In accordance with the present disclosure, echinocytes contained in blood can be detected from a visible absorption spectrum acquired for the blood. Thus, the present disclosure can be used typically for diagnosing a variety of diseases each known as disease in which echinocytes appear in blood at the start of the disease, for evaluating the quality of stored blood and for monitoring a drug therapy. In addition, the blood analysis apparatus according to the embodiment of the present disclosure can be used, for example, as an extracorporeal circulation dialysis machine, a blood gas inspection apparatus, a blood clotting evaluation apparatus or an occult blood tester, to mention a few.

The present disclosure contains subject matter related to that disclosed in Japanese Priority Patent Application JP 2011-172741 filed in the Japan Patent Office on Aug. 8, 2011, the entire content of which is hereby incorporated by reference.

It should be understood by those skilled in the art that various modifications, combinations, sub-combinations and alterations may occur depending on design requirements and other factors insofar as they are within the scope of the appended claims or the equivalents thereof.

What is claimed is:

1. A blood analysis apparatus, comprising:
    a light source configured to radiate visible light to a sample of blood;
    at least one lens to converge light reflected by the blood;
    a spectroscope configured to acquire a visible absorption spectrum based on the converged light;
    circuitry configured to
        detect a peak between a Soret absorption band and a Q absorption band in the visible absorption spectrum, wherein the peak is detected at a protruding edge of echinocytes in the blood,
        identify presence of the echinocytes in the blood based on the detection of the peak between the Soret absorption band and the Q absorption band in the visible absorption spectrum;
        determine that the peak indicates a heme structure distortion caused by change in a location of globin present in the blood, wherein the heme structure distortion further indicates the presence of the echinocytes; and
        control a display device to display a result of the detection of the peak and the presence of the echinocytes.

2. The blood analysis apparatus according to claim 1, wherein the circuitry is further configured to detect the peak that appears in a wavelength region of about 472 nm to identify the presence of the echinocytes.

3. The blood analysis apparatus according to claim 1, wherein the circuitry is further configured to control the display device to display that the peak is detected.

4. The blood analysis apparatus according to claim 1, wherein the circuitry is further configured to control the display device to display that the echinocytes exist in the blood.

5. The blood analysis apparatus according to claim 1, wherein the circuitry is further configured to control print of the result of the detection of the peak and the presence of the echinocytes.

6. The blood analysis apparatus according to claim 1, wherein the circuitry is further configured to store a standard spectrum to compare the standard spectrum and the visible absorption spectrum to identify difference in spectrum shape.

7. The blood analysis apparatus according to claim 1, wherein the circuitry is further configured to identify normal blood cells, that change into the echinocytes after a time period, based on the detection of the peak between the Soret absorption band and the Q absorption band in the visible absorption spectrum.

* * * * *